United States Patent [19]

Getz

[11] 4,219,331
[45] Aug. 26, 1980

[54] DENTAL IMPLEMENT
[76] Inventor: Edwin H. Getz, 60 Olive Pl., Forest Hills, N.Y. 11375
[21] Appl. No.: 972,779
[22] Filed: Dec. 26, 1978
[51] Int. Cl.² .............................................. H61C 5/12
[52] U.S. Cl. ...................................... 433/140; 433/31
[58] Field of Search ............... 32/69; 128/10; 350/308

[56] References Cited
U.S. PATENT DOCUMENTS

| | | | |
|---|---|---|---|
| 1,246,693 | 11/1917 | Wolfe | 128/10 |
| 1,844,733 | 2/1932 | Wise | 32/69 |
| 3,333,340 | 8/1967 | Boisvert | 32/33 |
| 4,024,642 | 5/1977 | Zorovich | 32/33 |

*Primary Examiner*—Robert Peshock
*Attorney, Agent, or Firm*—Darby & Darby

[57] ABSTRACT

A dental implement is disclosed which consists of a lip and cheek depressor or retractor adapted for mounting on the shank of a dental instrument adjacent the work portion of the instrument, such as a mirrored surface. The retractor is mounted for rotation about the longitudinal axis of the shank and may be detachably affixed thereto to facilitate interchangeability of retractors of various sizes and shapes.

7 Claims, 7 Drawing Figures

U.S. Patent      Aug. 26, 1980      4,219,331
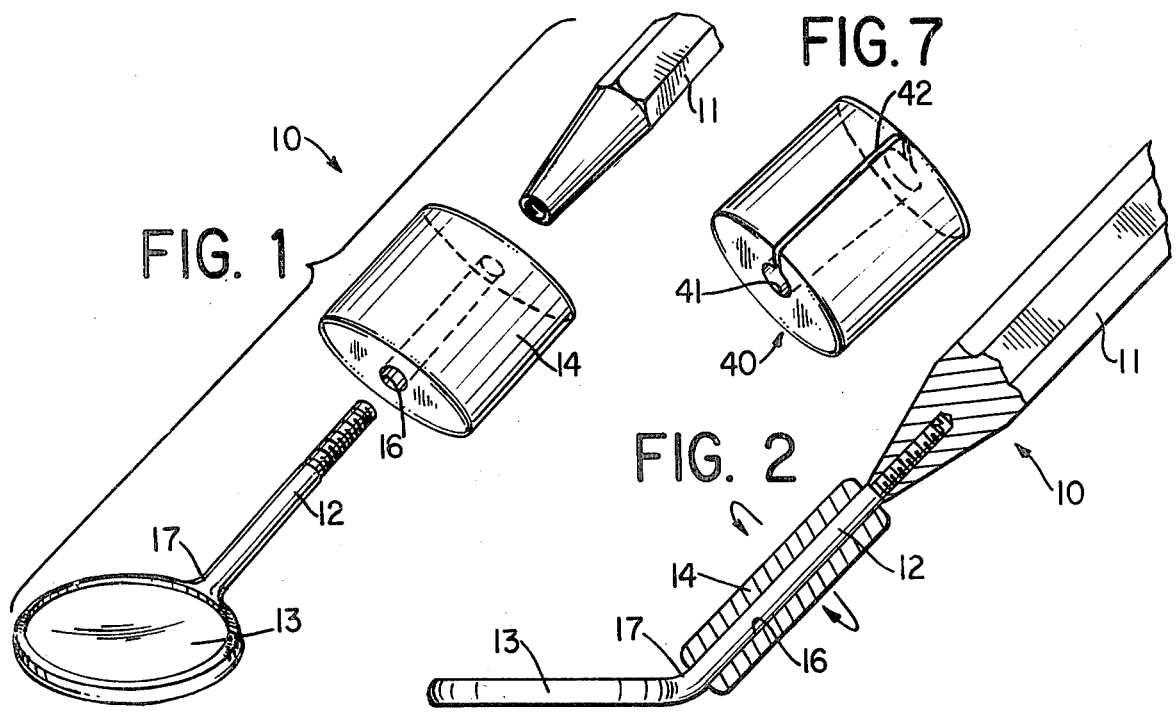
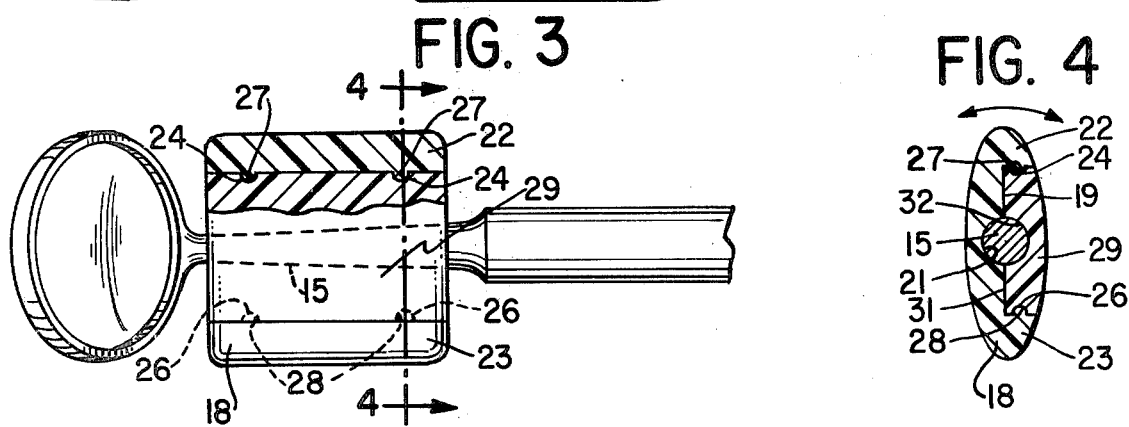
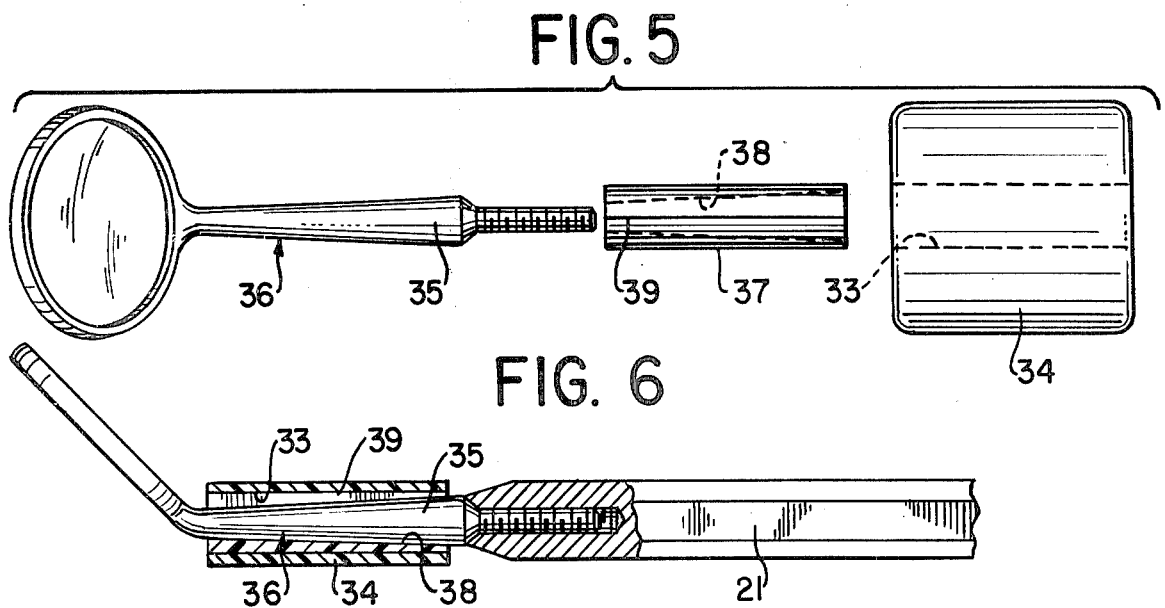

DENTAL IMPLEMENT

BACKGROUND OF THE INVENTION

The present invention relates to dental implements and in particular, to a retractor attachment for engaging the inner surface of the lip or cheek of a patient to press the lip or cheek outwardly so as to improve visibility within the patient's mouth. The attachment is particularly suitable for use with dental mirror instruments having a handle and shank portion connected to a generally wafer-like mirrored surface. The retractor attachment is rotatably mounted on the shank of the instrument adjacent the mirror and is adapted to press outwardly against the nearby lip or cheek surface within a patient's mouth to facilitate illumination and visibility of the work area imaged by the mirror. The retractor has an enlarged surface area for engaging the cheek and which extends transverse to the axis of the handle and shank and preferably substantially equidistantly on opposite sides thereof. When the cheek is engaged by the retractor, the shank (with the mirror) may be turned on its axis relative to the retractor to adjust the position of the mirror for optimum field of view without affecting the orientation of the retractor.

Heretofore, a variety of retractor elements have been utilized in connection with a dental mirror for the purpose of holding back the lip or cheek of a patient from a work area to be imaged by the mirror. Examples of these prior retractors are disclosed in U.S. Pat. Nos. 1,029,258 to Beadles, 1,844,733 to Wise and 2,582,121 to Harvey. These prior devices, however, suffer a distinct disadvantage in that the retractor of each is non-rotatably fixed to the shank of the dental mirror instrument. The fixed mounting limits the field of vision achievable during use of the dental instrument since the mirror position cannot be adjusted to improve the vision without simultaneously affecting the position of the retractor and therefore, its effectiveness. Unfortunately it often occurs that for these prior devices the most advantageous mirror position does not correspond to the most effective position of the retractor. Moreover, since minor necessary adjustments in the position of the mirror have heretofore effected corresponding changes in the retractor position, discomfort to the patient results as the protruding edges of the retractor tend, under these circumstances, to be pressed into the cheek or lip tissue.

BRIEF DESCRIPTION OF THE DRAWINGS:

For a further understanding of the present invention, reference may be had to the accompanying drawings in which:

FIG. 1 is an exploded perspective view of a dental implement in accordance with the present invention.

FIG. 2 is a side elevational view with parts broken away, of the device shown in FIG. 1;

FIG. 3 is a top view of an alternate embodiment showing a snap-on retractor;

FIG. 4 is a section taken along the line 4—4 of FIG. 3;

FIG. 5 is an exploded view of another embodiment of the invention;

FIG. 6 is a side elevational view with parts broken away of the embodiment of FIG. 5 as assembled.

FIG. 7 is a perspective view of another embodiment of a snap-on retractor.

BRIEF DESCRIPTION OF THE PREFERRED EMBODIMENTS

Referring now to the drawings, and in particular to FIG. 1, there is shown an exploded view of the components of a dental mirror instrument 10 for example, which includes a handle portion 11 adapted to engage a threaded shank 12 to which a standard wafer-type mirror 13 is attached.

A unitary retractor or depressor attachment 14 is adapted to be secured rotatably to the shank 12. In the present embodiment, the retractor has a substantially square configuration in the longitudinal plane and a substantially oval cross-section. The external circumferential surface area of the retractor is preferably smoothly and continuously rounded to avoid sharp edges which might injure the patient. A bearing channel or bore 16 is preferably centrally located and traverses the retractor longitudinally from one end to the other. The diameter of the bore 16 is slightly greater than the diameter of the shank 12 so as to receive the shank somewhat loosely to permit the retractor to rotate freely around the axis of the shank.

The instrument 10 is assembled, as shown in FIG. 2, by slipping the threaded end of the shank through the bore 16 of the retractor and then tightening the shank to the handle 11. The retractor element is of course shorter than the shank 12 so that the threaded portion of the shank extends beyond the retractor for insertion into the handle 11. The retractor is thus rotatably secured between the handle 11 and the mirror 13.

For the particular dental instrument exemplified in the drawings, the shank 12 for that portion immediately adjacent the mirror 13 is shown to flare outwardly to blend smoothly into the periphery of the mirror. Where the diameter of the bore 16 is uniform along its length, an outward flare of the shank adjacent the mirror would serve to locate the retractor so as to define a gap or space 17 between it and the mirror to prevent the retractor from abutting against the mirror and thereby interrupting its rotational capacity. Alternatively, such a spacing between the mirror and retractor can be established and maintained for other dental mirror styles by a variety of techniques known to those skilled in the art. For example, a conventional spacer or washer (not shown) may be fitted onto the shank 12 between the mirror and the retractor to retain the retractor away from the mirror so that it might rotate freely.

In operation, the instrument 10 with attached retractor 14 is inserted into the patient's mouth and the retractor is placed for example against the patient's cheek adjacent the work area so as to hold back the cheek to enable additional light to reach the work area. The rotatable mounting allows the dentist to vary his field of vision by rotating the handle 11 and attached mirror 13 while the retractor remains in a fixed position against the side of the mouth.

The bore 16 through the retractor 14 is dimensionally adapted to allow sliding the retractor longitudinally onto cylindrical shanks such as the shank 12. However, shanks tapered for example with decreasing diameter toward the mirror end, such as the shank 15 shown in FIG. 3, present a special problem since a straight bore with a diameter large enough to allow insertion of the larger end of the shank would result in a loose fit between the retractor and the shank at the relatively narrow portion of the shank adjacent to the mirror. Such a loose fit would permit undesirable wobble of the retractor.

Although a retractor with such a wobble can be used, it is desirable to eliminate the wobble. Accordingly, the present invention includes within its scope various alternative retractor structures which may be adapted to fit a tapered shank, such as the shank 15, in such a way as to eliminate wobbling. For example, with reference to FIGS. 3 and 4, a two-part retractor may be provided which includes a base member 18 having a longitudinal flat portion 19 in which is formed an exterior longitudinally tapering groove 21 of a configuration which substantially corresponds to the configuration of the tapered shank 15. A pair of raised edges or flanges 22 and 23 are formed on the base member along opposite sides of the flat 19 and extend along the length of the retractor substantially parallel to the groove 21. In the present embodiment, each of the flanges is provided with one or more laterally inwardly protruding nipples 24 and 26. The nipples are adapted to engage corresponding indentations 27 and 28 formed in opposite edges of a removably insertable clip member 29 having a flat portion 31 corresponding to the flat 19. The flat 31 is similarly provided with a longitudinal groove 32 adapted to receive the tapered shank 15 as shown in FIG. 4.

This embodiment of the lip and cheek retractor is assembled by placing the shank 15 within the groove 21 of the base member 18. The clip member 29 is placed over the shank and is inserted between the flanges 22 and 23 such that its groove 32 faces inwardly to accept the protruding portion of the shank. The clip member is then snapped onto the base member with the nipples 24 and 26 engaging the indentations 27 and 28 so as to retain or sandwich the shank between the base member and the clip. The dimensions of the opposing grooves 21 and 32 are such as to enable the assembled retractor to rotate freely on the shank 15.

It will be evident that the clip member 29 and base member 18 of such a two-piece retractor can take a variety of different cooperating shapes or configurations without departing from the scope of the invention. For example, each of such members may be provided with one of the flanges 22 or 23 such that it is the mirror image of the other. Such similarly shaped members would have an advantage in that only one mold would be required for manufacture of the elements of the two part retractor, thereby effecting manufacturing economies. It will also be evident that such a clip-on retractor is well suited for use with either cylindrical or tapered shanks and in connection with more modern dental oral instruments having a one-piece construction, as shown particularly in FIG. 3. In this type of instrument, the retractor can be attached onto the mirror shank 15, even though permanent bonding of the mirror head to the handle precludes subsequent attachment of bored retractors of the type shown in FIG. 1. Since other convenient clip-on configurations for the retractor may be utilized to provide a rotatable mounting on the shank of a mirror or other instrument, the specific configurations described above are set forth merely by way of example and are not intended to be exhaustive.

Another arrangement for mounting a retractor of the general type disclosed herein onto the tapered shank of a multi-part dental instrument is shown in FIGS. 5 and 6. As explained above, a straight cylindrical bore 33 in a retractor 34, similar to the retractor 14 of FIG. 1 and sufficient to allow passage of the large diameter portion 35 of a tapered shank 36 through the retractor, would result in undesirable wobbling of the retractor. Accordingly, an adaptor bushing 37 may be provided to enable the use of a retractor having a uniform bore dimension. The bushing 37 is preferably a substantially cylindrical element made of suitably lightweight, low friction and resilient material, and having an internal longitudinal bore 38 the configuration of which corresponds substantially to that of the tapered instrument shank 36 for which it is adapted. The bushing 37 is also provided with a longitudinal slit 39 through its side wall to enable it to be laterally snapped over and onto the tapered instrument shank. Where the bushing material is suitably resilient, such as through the use of an elastic material, it may be snapped over the shank without being permanently deformed. The dimensions of the uniform longitudinal bore 33 in the retractor 34 may be only slightly greater than those of the external surface area of the bushing 37 to enable a snug non-rotatable fit of the latter therein. Under these circumstances, the bushing 37 will rotate on the shank 36 and carry the retractor with it. Alternatively, the bushing 37 may be adapted to fit both the shank 36 non-rotatably and the retractor bore 33 loosely to enable the retractor to rotate thereon. After the bushing is snapped onto the tapered shank, the shank and bushing are inserted into the bore 33 through the retractor and the instrument handle 21 is thereafter attached to the shank as shown in FIG. 6.

In many circumstances, it will be preferable to eliminate the bushing and to provide a retractor, such as the retractor 40 shown in FIG. 7, with a central longitudinal bore 41, which may or may not be tapered depending upon the instrument shank to which it is to be attached, communicating with a radial and longitudinally extending slot 42 opening to the exterior of the retractor. In this embodiment the retractor is constructed of suitably resilient or elastic material. Under these circumstances, the instrument shank can then be inserted into the bore 41 by pressing the slot 42 open, inserting the shank laterally and permitting the retractor to snap back into position around the shank, owing to the natural resiliency of the material. By providing a bore corresponding to and slightly larger than the shank, free rotation of the retractor can be achieved as described above. This arrangement offers the advantage of quick and easy removal or interchangeability of retractors as desired. It also simplifies and economizes commercial production techniques in that it is of one-piece moldable construction.

Although the retractor of the present invention has been illustrated as having a substantially rectangular shape, it should be understood that it may take a variety of different shapes, as desired, in order to achieve the results required by the dentist in a particular situation. For example, the retractor may extend behind the mirror if necessary. Although such an extended retractor might prevent a full 360° rotation relative to the mirror it will still allow for limited rotation. It has been found that under some circumstances rotation through approximately 2°–3° will enable the mirror to be adjusted to enhance adequately the dentist's field of vision.

It will be apparent to those skilled in the art that the present invention may take a variety of forms and that the foregoing description is merely illustrative. Accordingly, the scope of protection afforded this invention is not to be limited except as defined by the following claims.

What is claimed is:

1. A device for retracting the lip or cheek of a patient away from a work area during use of a dental instrument in the mouth of the patient comprising; a depressor member mounted on the instrument such that said member is free to rotate on the instrument independently thereof, said member having an enlarged external surface area transverse to the instrument, said area being adapted to engage the inside of the mouth of the patient while the instrument is being used thereby to widen the mouth to improve visibility therein.

2. The device of claim 1 in which the depressor is provided with a longitudinal bore substantially parallel to said surface area, said bore being adapted to receive a corresponding portion of the instrument.

3. The device of claim 2 in which said depressor is detachably mounted on the instrument.

4. The device of claim 3 in which the depressor is formed of elastic material and includes a longitudinal and radially inwardly extending slot coextensive with and opening into said bore, the width of said slot being less than the diameter of said instrument portion.

5. The device of claim 2 in which said depressor is mounted for rotation about the longitudinal axis of the instrument.

6. The device of claim 5 comprising in addition a bushing element within said bore and engaging said portion of the instrument.

7. The device of claim 1 in which said depressor comprises:
   a clip member;
   a base member having a lengthwise internal groove adapted for rotatable engagement with a corresponding portion of the instrument; and
   means for connecting said clip member to said base member with said instrument portion therebetween.

* * * * *